(12) United States Patent
Ravuna et al.

(10) Patent No.: US 10,684,986 B2
(45) Date of Patent: Jun. 16, 2020

(54) DOUBLE BUFFERING WITH ATOMIC TRANSACTIONS FOR THE PERSISTENT STORAGE OF REAL-TIME DATA FLOWS

(71) Applicant: BIOSENSE WEBSTER (ISRAEL) LTD., Yokneam (IL)

(72) Inventors: Eliyahu Ravuna, Kiryat Ata (IL); Goren Cohn, Haifa (IL); Roey Lehman, Kiryat Bialik (IL); Yochai Alon Timmer, D.N. Hof Ashkelon (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 14/011,796

(22) Filed: Aug. 28, 2013

(65) Prior Publication Data

US 2015/0067000 A1 Mar. 5, 2015

(51) Int. Cl.
*G06F 16/13* (2019.01)
*G06F 3/06* (2006.01)
(Continued)

(52) U.S. Cl.
CPC .............. *G06F 16/13* (2019.01); *G06F 3/061* (2013.01); *G06F 3/0656* (2013.01);
(Continued)

(58) Field of Classification Search
CPC ..... G06F 2003/0691; G06F 2003/0692; G06F 5/16; G06F 5/065; G06F 7/78;
(Continued)

(56) References Cited

U.S. PATENT DOCUMENTS 5,163,132 A 11/1992 DuLac et al.
5,391,199 A 2/1995 Ben-Haim
(Continued)

FOREIGN PATENT DOCUMENTS

CN 1168625 A 12/1997
CN 1956088 A 5/2007
(Continued)

OTHER PUBLICATIONS

Jenkov (Jenkov, j. "Java Concurrency: Read/Write Locks," 2008, https://dzone.com/articles/java-concurrency-read-write-lo).*
(Continued)

*Primary Examiner* — Tracy A Warren
(74) *Attorney, Agent, or Firm* — Notaro, Michalos & Zaccaria P.C.

(57) ABSTRACT

A method, including configuring, in a memory, a first buffer to store first buffer data, a second buffer to store second buffer data, and a variable indicative of a persisted size of real-time data persisted to a storage device. On the storage device, a file is configured to store the real-time data and a field is configured to store the variable. A stream of the real-time data is received, and the stream is appended to the first buffer data. Upon meeting a write criteria, the first buffer data in is swapped with the second buffer data, a buffer size of the second buffer data is added to the variable, and the second buffer data is conveyed from the second buffer to a write cache. Upon meeting a commit criteria, the stream stored in the write cache is appended to the file, and the variable is persisted to the field.

23 Claims, 5 Drawing Sheets

(51) Int. Cl.
*G16H 30/40* (2018.01)
*G16H 30/20* (2018.01)

(52) U.S. Cl.
CPC ........... *G06F 3/0674* (2013.01); *G16H 30/20* (2018.01); *G16H 30/40* (2018.01)

(58) Field of Classification Search
CPC ........... G06F 9/30123; G06F 2205/062; G06F 2205/063; G06F 2205/066; G06F 2205/067; G06F 2212/6022; G06F 2212/7203
USPC ............. 711/171, 502, 507–509, 522, 213
See application file for complete search history.

(56) References Cited

U.S. PATENT DOCUMENTS

| | | | |
|---|---|---|---|
| 5,443,489 A | | 8/1995 | Ben-Haim |
| 5,497,487 A | * | 3/1996 | Fortier ................. G06F 11/1474 |
| 5,558,091 A | | 9/1996 | Acker et al. |
| 5,686,960 A | | 11/1997 | Sussman |
| 5,944,022 A | | 8/1999 | Nardella et al. |
| 5,983,126 A | | 11/1999 | Wittkampf |
| 6,100,906 A | | 8/2000 | Asaro et al. |
| 6,172,499 B1 | | 1/2001 | Ashe |
| 6,177,792 B1 | | 1/2001 | Govari et al. |
| 6,456,864 B1 | | 9/2002 | Swanson et al. |
| 6,690,963 B2 | * | 2/2004 | Ben-Haim ............... A61N 1/32 600/117 |
| 6,701,341 B1 | * | 3/2004 | Wu ...................... A61B 5/0456 128/915 |
| 6,788,967 B2 | | 9/2004 | Ben-Haim et al. |
| 7,184,442 B1 | * | 2/2007 | Roos .................... H04J 3/0632 370/412 |
| 7,853,568 B2 | | 12/2010 | Mukhi |
| 2002/0078284 A1 | | 6/2002 | Mckenney |
| 2004/0250039 A1 | | 12/2004 | Hanks |
| 2006/0195704 A1 | * | 8/2006 | Cochran .............. G06F 11/1666 713/193 |
| 2007/0297433 A1 | * | 12/2007 | Lin ..................... G06F 13/4059 370/412 |
| 2008/0288496 A1 | | 11/2008 | Duggirala et al. |
| 2009/0093806 A1 | | 4/2009 | Govari et al. |
| 2009/0138007 A1 | | 5/2009 | Govari et al. |
| 2010/0125695 A1 | * | 5/2010 | Wu ....................... G06F 3/0613 711/103 |
| 2010/0333096 A1 | * | 12/2010 | Dice ...................... G06F 12/00 718/102 |
| 2011/0246503 A1 | | 10/2011 | Bender et al. |

FOREIGN PATENT DOCUMENTS

| | | |
|---|---|---|
| CN | 101097503 A | 1/2008 |
| EP | 1785836 A2 | 5/2007 |
| JP | 06-095936 | 4/1994 |
| JP | 08-179977 A | 7/1996 |
| JP | 2000-347909 A | 12/2000 |
| JP | 2006113927 A | 4/2006 |
| JP | 2010-122761 A | 6/2010 |
| JP | 2012-038262 A | 2/2012 |

OTHER PUBLICATIONS

European Search Report dated Jul. 9, 2015 for corresponding Application No. EP14182533.
Extended search report of corresponding European patent application No. EP 14182533.1, dated Nov. 9, 2015.
Office Action and Search Report for corresponding Chinese patent application No. 201410432688.0, dated Jun. 11, 2018.
Japanese office action for corresponding Japanese application No. JP 2014-172375, dated Sep. 4, 2018.
Australian examination report for corresponding Australian application No. AU 2014215988, dated Feb. 28, 2019.
Extended European Search Report for corresponding European patent application No. 19157783.2, dated Aug. 5, 2019.

* cited by examiner

DOUBLE BUFFERING WITH ATOMIC TRANSACTIONS FOR THE PERSISTENT STORAGE OF REAL-TIME DATA FLOWS

FIELD OF THE INVENTION

The present invention relates generally to processing real-time data, and specifically to using double buffering with atomic transactions to process real-time electrophysiological data.

BACKGROUND OF THE INVENTION

A wide range of medical procedures involve placing objects, such as sensors, tubes, catheters, dispensing devices, and implants, within a patient's body. Real-time imaging methods are often used to assist doctors in visualizing the object and its surroundings during these procedures. In most situations, however, real-time three-dimensional imaging is not possible or desirable. Instead, a medical system configured to obtain real-time spatial coordinates of the internal object is often utilized.

During a medical procedure, the medical system may collect real-time electrophysiological (EP) data comprising analog EP data and/or digital EP data. Examples of analog EP data include, but are not limited to, voltage and current of electrodes, body temperature of a patient and data collected from other sensors. Examples of digital EP data include, but are not limited to, digital data provided by other systems and results of signal processing calculations, such as a spatial location of catheters and a status of the patient's respiration.

The description above is presented as a general overview of related art in this field and should not be construed as an admission that any of the information it contains constitutes prior art against the present patent application.

SUMMARY OF THE INVENTION

There is provided, in accordance with an embodiment of the present invention a method for storing real-time data, including configuring, in a memory, a first buffer to store first buffer data, a second buffer to store second buffer data, and a variable indicative of a persisted size of the real-time data persisted to a storage device, configuring, on the storage device, a file to store the real-time data and a field to store the variable, receiving, by a processor, a stream of the real-time data, and appending the stream of the real-time data to the first buffer data. The method also includes, upon meeting a write criteria, swapping the first buffer data in the first buffer with the second buffer data in the second buffer, adding a buffer size of the second buffer data in the second buffer to the variable, and calling a write function to convey the second buffer data from the second buffer to a write cache. The method further includes, upon meeting a commit criteria, calling a commit function to append the stream of the real-time data stored in the write cache to the file, and persisting the variable to the field.

In some embodiments, the real-time data may include electrophysiological (EP) data collected while performing a medical procedure. In additional embodiments, the EP data may be selected from analog data and digital data. In further embodiments, the analog data may be selected from a list including voltages, currents and temperatures. In supplementary embodiments, the digital data may be selected from a list including image data, position measurements, force measurements, and respiration statuses.

In additional embodiments, the first buffer may be stored at a first address in the memory and the second buffer may be stored at a second address in the memory, and wherein swapping the first buffer data in the first buffer with the second buffer data in the second buffer includes toggling a buffer address stored in a buffer pointer between the first and the second addresses, thereby switching roles of the first and the second buffers.

In further embodiments, the method may include configuring a first reader-writer lock to protect the first buffer and a second reader-writer lock to protect the second buffer and the variable. In some embodiments including the first and the second reader locks, the method may include acquiring a writer lock for the first reader-writer lock prior to appending the stream of the real-time data, and releasing the writer lock from the first reader-writer lock subsequent to appending the stream of the real-time data. In additional embodiments including the first and the second reader locks, the method may include acquiring a first writer lock for the first reader-writer lock and a second writer lock for the second reader-writer lock upon meeting the write criterion and prior to swapping the first and the second buffers, and releasing the first and the second writer locks upon swapping the first buffer data in the first buffer with the second buffer data in the second buffer.

In further embodiments including the first and the second reader locks, the method may include acquiring a writer lock for the second reader-writer lock subsequent to calling the write function and prior to adding the buffer size to the variable, clearing the second buffer, and releasing the writer lock upon clearing the second buffer. In supplementary embodiments including the first and the second reader locks, persisting the variable to the field may include acquiring a reader lock for the second reader-writer lock, copying the variable to an additional variable, releasing the reader lock, and storing the additional variable to the field.

In additional embodiments including the first and the second reader locks, upon receiving a request to retrieve a range of the real-time data, the method may include calculating a range size for the range, configuring, in the memory, a response buffer, acquiring a first reader lock for the first reader-writer lock and a second reader lock for the second reader-writer lock, copying first data including an intersection of the range and the first buffer to the response buffer, the first data having a first size, prepending second data including an intersection of the range and the second buffer to the response buffer, the second data having a second size, releasing the first and the second reader locks, and upon the range size being greater than a sum of the first and the second sizes, retrieving, from the write cache and the storage device, third data including a complement of the range and fourth data including the first data and the second data, and prepending the third data to the response buffer.

In further embodiments, the method may include configuring a first reader-writer lock to protect the first buffer, a second reader-writer lock to protect the second buffer and a third reader-writer lock to protect the variable. In some embodiments including the first, the second and the third reader locks, the method may include acquiring a writer lock for the first reader-writer lock prior to appending the stream of the real-time data, and releasing the writer lock from the first reader-writer lock subsequent to appending the stream of the real-time data. In additional embodiments including the first, the second and the third reader locks, the method may include acquiring first writer lock for the first reader-writer lock and a second writer lock for the second reader-writer lock upon meeting the write criterion and prior to swapping the first buffer data in the first buffer with the second buffer data in the second buffer, and releasing the first and the second writer locks upon swapping the first buffer data in the first buffer with the second buffer data in the second buffer.

In further embodiments including the first, the second and the third reader locks, the method may include acquiring a first writer lock for the second reader-writer lock and a second writer lock for the third reader-writer lock subsequent to calling the write function and prior to adding the buffer size to the variable, clearing the second buffer, and releasing the first and the second writer locks upon clearing the second buffer. In supplementary embodiments including the first, the second and the third reader locks, persisting the variable to the field may include acquiring a reader lock for the third reader-writer lock, copying the variable to an additional variable, releasing the reader lock, and storing the additional variable to the field.

In supplementary embodiments including the first, the second and the third reader locks, upon receiving a request to retrieve a range of the real-time data, the method may include calculating a range size for the range, configuring, in the memory, a response buffer, acquiring a first reader lock for the first reader-writer lock and a second reader lock for the second reader-writer lock, copying first data including an intersection of the range and the first buffer to the response buffer, the first data having a first size, prepending second data including an intersection of the range and the second buffer to the response buffer, the second data having a second size, releasing the first and the second reader locks, and upon the range size being greater than a sum of the first and the second sizes, retrieving, from the write cache and the storage device, third data including a complement of the range and fourth data including the first data and the second data, and prepending the third data to the response buffer.

There is also provided, in accordance with an embodiment of the present invention an apparatus for storing real-time data, including An apparatus for storing real-time data, including a storage device configured to store a file, and to store a field indicative of a persisted size of the real-time data persisted to the file, a memory arranged to store a first buffer configured to store first buffer data, a second buffer configured to store second buffer data, and to store a variable indicative of the persisted size, and a processor configured to receive a stream of the real-time data, and to append the stream of the real-time data to the first buffer data. Upon meeting a write criteria, the processor is also configured to swap the first buffer data in the first buffer with the second buffer data in the second buffer, to add a buffer size of the second buffer data in the second buffer to the variable, and to call a write function configured to convey the second buffer data from the second buffer to a write cache. Upon meeting a commit criteria, the processor is further configured to call a commit function configured to append the stream of the real-time data stored in the write cache to the file, and to persist the variable to the field.

There is further provided, in accordance with an embodiment of the present invention, a computer software product the product including a non-transitory computer-readable medium, in which program instructions are stored, which instructions, when read by a computer, cause the computer to configure, in a memory, a first buffer to store first buffer data, a second buffer to store second buffer data, and a variable indicative of a persisted size of real-time data persisted to a storage device, to configure, on the storage device, a file to store the real-time data and a field to store the variable, to receive a stream of the real-time data, and to append the stream of the real-time data to the first buffer data Upon meeting a write criteria, the instructions also cause the computer to swap the first buffer data in the first buffer with the second buffer data in the second buffer, to add a buffer size of the second buffer data in the second buffer to the variable, and to call a write function to convey the second buffer data from the second buffer to a write cache. Upon meeting a commit criteria, the instructions additionally cause the computer to call a commit function to append the stream of the real-time data stored in the write cache to the file, and to persist the variable to the field.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

During a medical procedure such as cardiac ablation, there may be a continuous stream of real-time electrophysiological (EP) data that needs to be persisted to a persistent storage medium (also referred to herein as a storage device), such as a hard disk. Real-time EP data generally flows at a constant rate, although the rate may also change during the procedure. Because of the nature of medical data, the real-time EP data may be persisted to the storage medium in a transactional manner, so that in the event of a system failure or a power outage the system should be able to identify the last reliable byte in the persisted data stream.

Embodiments of the present invention provide methods and systems for implementing double buffering with atomic transactions to persistently store real-time EP data to a file on a persistent storage medium. In some embodiments, a random access memory (RAM) is configured to store two data buffers and variable storing, and a persistent storage medium is configured to store the file and a field. As explained hereinbelow, the field can store a first size of the real-time data persisted to the storage medium and the variable can store the first size of the real-time data persisted to the storage medium plus a second size of the real-time data stored in one of the buffers that is scheduled to be destaged to the storage medium. Additionally, a first reader-writer (RW) lock can be configured to protect a first of the buffers, and a second RW lock can be configured to protect a second of the buffers and the variable.

Upon receiving a stream of real-time EP data, the stream can be appended to the first buffer. Periodically, as explained hereinbelow, the stream of real-time EP data accumulated in the first buffer can be transferred to a write cache by first swapping the first and the second buffers, updating the variable, and calling a write function to convey the data from the second buffer to the write cache. To persist the data stored in the write cache to the persistent storage medium, a commit function can be called to destage the real-time EP data from the cache to the persistent storage medium, the value the in the variable can be conveyed to the write cache, and the commit function can be called a second time to destage the value from the write cache to the field on the storage device.

Embodiments of the present invention enable streams of real-time EP data to be continuously processed without encountering any delay caused by any locks protecting system resources. Additionally, embodiments of the present invention enable processing read requests without encountering any delay caused by any lock waiting, as long as the real-time EP data is still stored in any of the buffers. Furthermore, a system implementing embodiments of the present invention can ensure that "chunks" of real-time EP data are committed in atomic transactions even if the chunks are destaged to the storage device in a different order than the order that the data was conveyed to the write cache.

System Description

Figure 1:
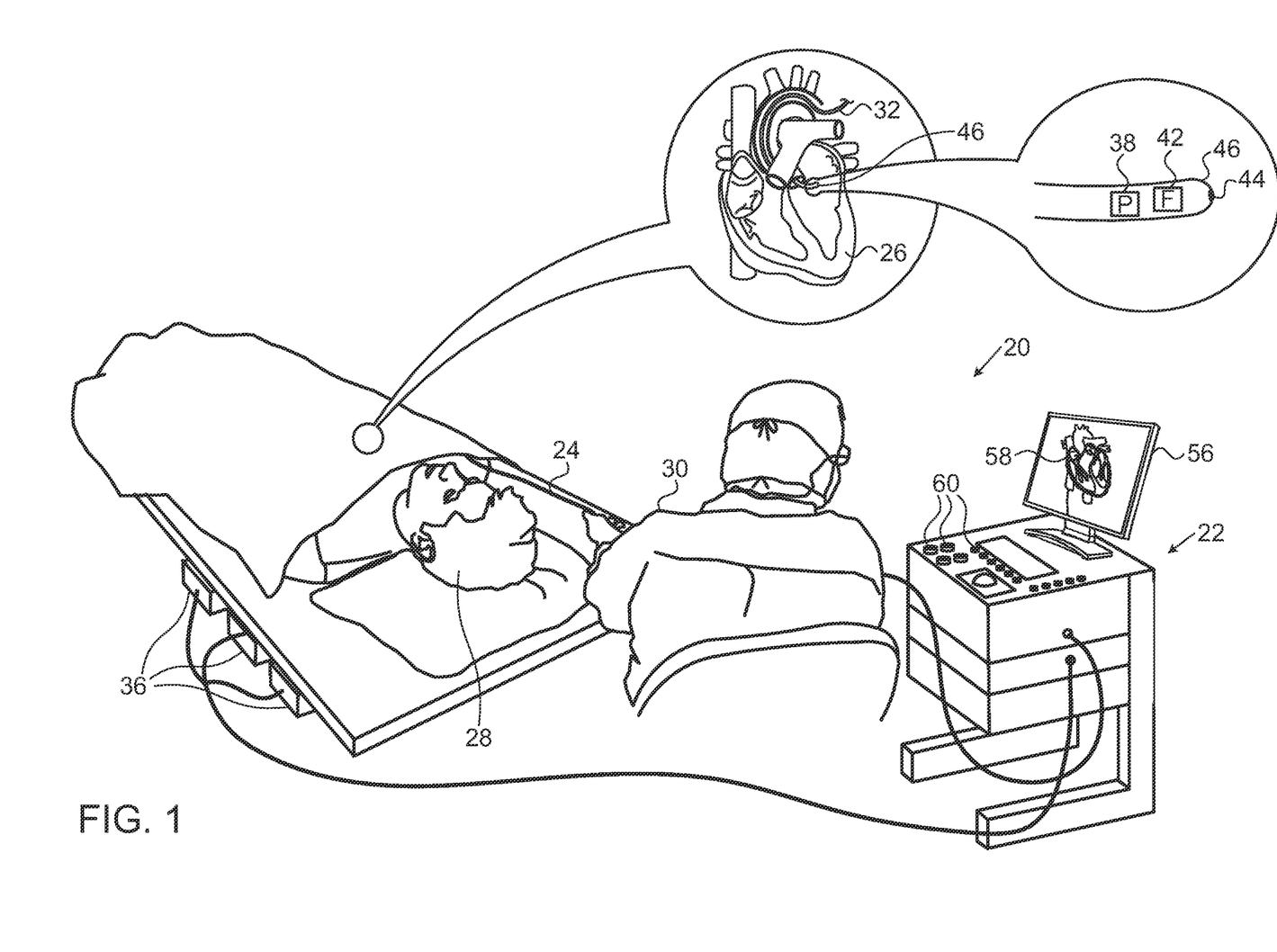
FIG. 1 is a schematic, pictorial illustration of a medical system having a console configured to implement double buffering with atomic transactions for persistent storage of real-time electrophysiological (EP) data, in accordance with an embodiment of the present invention.
Figure 2:
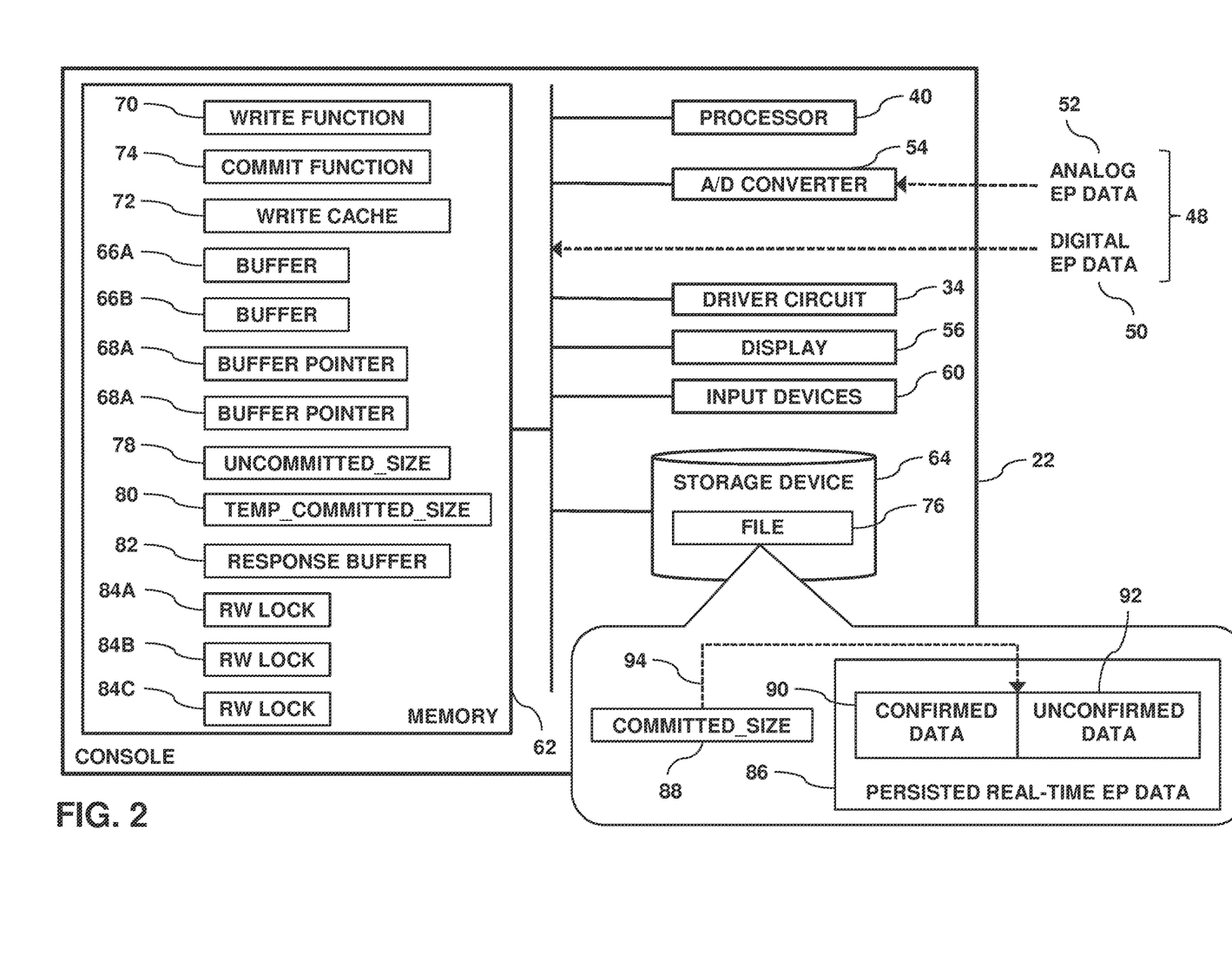
FIG. 2 is a block diagram of the console, in accordance with an embodiment of the present invention.

FIG. 1 is a schematic, pictorial illustration of a medical system 20 comprising a control console 22 that implements double buffering with atomic transactions for persistent storage of real-time electrophysiological (EP) data, and FIG. 2 is a block diagram of the console, in accordance with an embodiment of the present invention. System 20 comprises control console 22 and a probe 24, such as an intracardiac catheter. In embodiments described hereinbelow, it is assumed that probe 24 is used for diagnostic or therapeutic treatment, such as for mapping electrical potentials in a heart 26 of a patient 28. Alternatively, probe 24 may be used, mutatis mutandis, for other therapeutic and/or diagnostic purposes in the heart or in other body organs.

An operator 30 inserts probe 24 through the vascular system of patient 28 so that a distal end 32 of probe 24 enters a chamber of heart 26. In the example shown in FIGS. 1 and 2, console 22 uses magnetic position sensing to determine position coordinates of distal end 32 inside heart 26. To determine the position coordinates, a driver circuit 34 in console 22 drives field generators 36 to generate magnetic fields within the body of patient 28. Typically, field generators 36 comprise coils, which are placed below the patient's torso at known positions external to patient 28. These coils generate magnetic fields in a predefined working volume that contains heart 26. A magnetic field sensor 38 (also referred to herein as position sensor 38) within distal end 32 of probe 24 generates electrical signals in response to these magnetic fields. A signal processor 40 processes these signals in order to determine the position coordinates of distal end 32, typically including both location and orientation coordinates. The method of position sensing described hereinabove is implemented in the CARTO™ mapping system produced by Biosense Webster Inc., of Diamond Bar, Calif. and is described in detail in the patents and patent applications cited hereinbelow.

Position sensor 38 transmits a signal to console 22 that is indicative of position of distal end 32. Position sensor 38 may comprise one or more miniature coils, and typically comprises multiple coils oriented along different axes. Alternatively, position sensor 38 may comprise either another type of magnetic sensor, or position transducers of other types, such as impedance-based or ultrasonic position sensors. Although FIG. 1 shows a probe with a single position sensor, embodiments of the present invention may utilize probes with more than one position sensor.

Although in the present example system 20 measures the position of distal end 32 using magnetic-based sensors, other position tracking techniques may be used (e.g., impedance-based sensors). Magnetic position tracking techniques are described, for example, in U.S. Pat. Nos. 5,391,199, 5,443,489, 6,788,967, 6,690,963, 5,558,091, 6,172,499 6,177,792, whose disclosures are incorporated herein by reference. Impedance-based position tracking techniques are described, for example, in U.S. Pat. Nos. 5,983,126, 6,456,864 and 5,944,022, whose disclosures are incorporated herein by reference.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

Probe 24 also comprises a force sensor 42 contained within distal end 32, and an electrode 44 coupled to the distal end. Force sensor 42 measures a force applied by a distal tip 46 of probe 24 to endocardial tissue of heart 26 by generating a signal to the console that is indicative of the force exerted by the distal tip on the endocardial tissue. In one embodiment, the force sensor may comprise a magnetic field transmitter and receiver connected by a spring in distal end 32, and may generate an indication of the force based on measuring the deflection of the spring. Further details of this sort of probe and force sensor are described in U.S. Patent Application Publications 2009/0093806 and 2009/0138007, whose disclosures are incorporated herein by reference. Alternatively, distal end 32 may comprise another type of force sensor.

In some embodiments, electrode 44 may be configured to function as an impedance-based position transducer. Additionally or alternatively, electrode 44 can be configured to measure a certain physiological property (e.g., the local surface electrical potential) at multiple locations on the endocardial tissue, and/or to deliver radio frequency (RF) energy to the endocardial tissue during an ablation procedure.

In embodiments described herein, processor 40 is configured to collect real-time electrophysiological (EP) data 48 comprising digital EP data 50 and analog EP data 52 that is received via an analog/digital (A/D) converter 54. Examples of digital EP data 50 include, but are not limited to, position measurements and force measurements from probe 24, respiration statuses for patient 28, and image data from a medical imaging system (not shown) such as a magnetic resonance imaging (MRI) system, or a computed tomography (CT) system. Examples of analog EP data 52 include, but are not limited to, voltages, currents and temperatures.

Processor 40 drives a display 56 to present operator 30 with an image 58 showing the position of distal end 32 in the patient's body, as well as status information and guidance regarding the procedure that is in progress. During a diagnostic treatment, image 58 may comprise a simulated surface of heart 26. In some embodiments, operator 30 can manipulate image 58 using one or more input devices 60.

Console 22 also comprises a random access memory (RAM) 62 and a storage device 64 such as a hard disk drive or a solid state disk drive. Storage device 64 may comprise more than one physical device. To implement double buffering memory 62 comprises buffers 66, and buffer pointers 68. In the description herein, buffers 66 and buffer pointers 68 may be differentiated by appending a letter to the identifying numeral, so that the buffers comprise buffers 66A and 66B, and the buffer pointers comprise buffer pointers 68A and 68B. As explained hereinbelow, upon receiving real-time EP data 48, processor 40 stores the received data to a given buffer 66 indicated by buffer pointer 68A.

Memory 62 also comprises a write function 70 that is configured to convey real-time EP data 48 from buffers 66 to a write cache 72, and a commit function 74 that is configured to destage the real-time EP data from the write cache to a file 76 on storage device 64. Memory 62 additionally comprises an uncommitted_size variable 78 indicative of a persisted size of the real-time EP data stored on storage device 64, a temp_committed_size variable 80, and a response buffer 82 whose operations are described hereinbelow.

Memory 62 further comprises reader-writer (RW) locks 84. In the description herein, RW locks 84 may be differentiated by appending a letter to the identifying numeral, so that the RW locks comprise reader-writer locks 84A, 84B and 84C. In embodiments of the present invention, system 20 can perform double buffering with atomic transactions by utilizing either two or three RW locks 84. RW locks 84 are configured to control client (e.g., an application executing on processor 40) access to resources in memory 62 such as buffers 66 and uncommitted_size 78, allowing concurrent access to multiple threads for reading but restricting access to a single thread for writes (or other changes) to the resource. In operation, processor 40 can acquire a reader lock or a write lock for a given RW lock 84.

A writer lock allows a first client to read from and to write to the resource it protects. Upon processor 40 acquiring a writer lock for a given RW lock 84 configured to protect a given resource, no additional reader or writer locks can be acquired for the given resource and all subsequent read and write requests of other clients are blocked until the first client releases the writer lock.

A reader lock grants the first client read-only access to the resource it protects. Upon processor 40 acquiring a reader lock for a given RW lock 84 configured to protect the given resource, additional reader locks can be acquired for the given resource, and read requests from other clients having reader locks on the given resource can be processed. While more than one reader lock can be acquired for a given resource, writer locks (and therefore any write requests) are blocked from the given resource until all clients release their reader locks.

File 76 comprises persisted real-time EP data 86 and a committed_size field 88. Persisted real-time EP data 86 comprises confirmed data 90 and unconfirmed data 92. As indicated by an arrow 94, committed_size 88 points to a last byte of confirmed data 90 whose persistence is confirmed by a completion of an atomic transaction, per embodiments described hereinbelow. Prior to completing a given atomic transaction by updating committed_size 88, unconfirmed data 92 comprises real-time data 48 that has been destaged from write cache 72 to file 76. Therefore, in the event of a system failure or a power failure, committed_size 88 points to a last byte in persisted real-time data EP 86 that can be reliably read. In other words, any persisted real-time EP data 86 stored in unconfirmed data 92 comprises real-time EP data 48 that may or may not be completely persisted (i.e., destaged) from write cache 72 to file 76 on storage device 64.

Processor 40 typically comprises a general-purpose computer, with suitable front end and interface circuits for receiving signals from probe 24 and controlling the other components of console 22. Processor 40 may be programmed in software to carry out the functions that are described herein. The software may be downloaded to console 22 in electronic form, over a network, for example, or it may be provided on non-transitory tangible media, such as optical, magnetic or electronic memory media. Alternatively, some or all of the functions of processor 40 may be carried out by dedicated or programmable digital hardware components.

Real-Time EP Data Processing

Figure 3A:
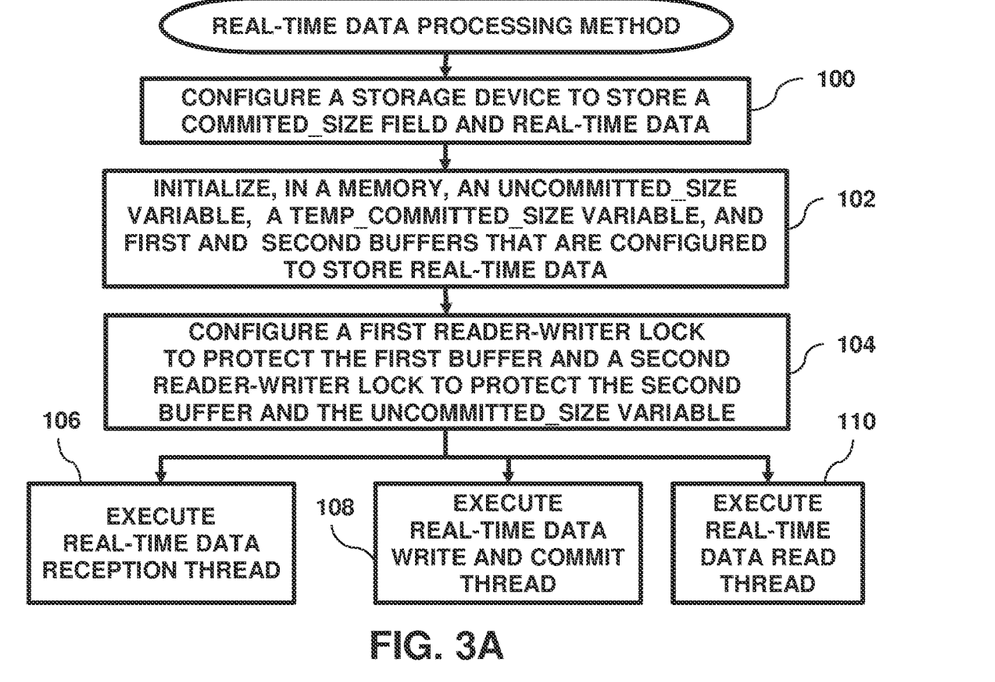
FIGS. 3A-3D, referred to collectively as FIG. 3, are flow diagrams that schematically illustrate a method of processing the real-time EP data, in accordance with an embodiment of the present invention.

FIG. 3A is a flow diagram that schematically illustrates a method of processing real-time EP data 48, in accordance with an embodiment of the present invention. While embodiments herein describe using double buffering and atomic transactions to processing real-time EP data 48 collected while performing a medical procedure, using double buffering and atomic transactions to process any other type of real-time data is considered to be within the spirit and scope of the present invention.

In a first configuration step 100, processor 40 configures storage device 64 to store file 76 and committed_size 88. While in the example shown in FIG. 2, persisted EP data 86 and committed_size 88 are stored in file 76, the real time EP data and the committed_size field may be stored in separate files on storage device 64.

In an initialization step 102, processor 40 initializes uncommitted_size 78 and temp_committed_size 80, and configures buffers 66 to store real-time EP data 48. To store real-time EP data 48, processor 40 configures the first buffer to store first buffer data and the second buffer to store second buffer data. Initially, uncommitted_size 78 and committed_size 88 store identical values that indicate an initial size of a data stream comprising data 48. Typically the initial size of the data stream is zero, but it can be greater than zero if the data stream has any header information.

While processing real-time EP data 48, buffers 66 are either empty or correspond to a specific range in file 76. In embodiments described herein, whenever the terms buffers 66 or a given buffer 66 are used, the terms refer both to the real-time EP data stored in the buffers and a corresponding range in file 76.

As described hereinbelow in FIG. 3B, processor 40 stores real-time EP data 48 to a given buffer 66 indicated by buffer pointer 68A. Therefore the given buffer currently indicated by buffer pointer 68A comprises an "active" buffer referred to herein as a first buffer, and the buffer currently not indicated by the buffer pointer comprises an "inactive" buffer referred to herein as a second buffer.

In embodiments herein, buffer pointer 68A always points to the first buffer, and pointer 68B always points to the second buffer. Therefore, if the first buffer comprises buffer 66A and the second buffer comprises buffer 66B, then buffer pointer 66A points to buffer 66A and buffer pointer 68B points to buffer 66B. Likewise, if the first buffer comprises buffer 66B and the second buffer comprises buffer 66A, then buffer pointer 66A points to buffer 66B and buffer pointer 68B points to buffer 66A. As explained hereinbelow, processor 40 can swap the first buffer and the second buffers by swapping a first address stored in buffer pointer 68A with a second address stored in buffer pointer 68B.

In a second configuration step 104, processor 40 configures lock 84A to protect the first buffer and configures lock 84B to protect the second buffer and uncommitted_size 78. In an alternative embodiment, processor 40 may configure lock 84A to protect the first buffer, configure lock 84B to protect the second buffer, and configure lock 84C to protect uncommitted_size 78.

Upon completing second configuration step 104, processor 40 can simultaneously execute one or more real-time data reception threads in a first execute step 106 (described in FIG. 3B hereinbelow), a single real-time data write and commit thread (as described in FIG. 3C hereinbelow) in a second execute step 108, and one or more real-time data read threads (as described in FIG. 3D hereinbelow) in a third execute step 110.

Figure 3B:
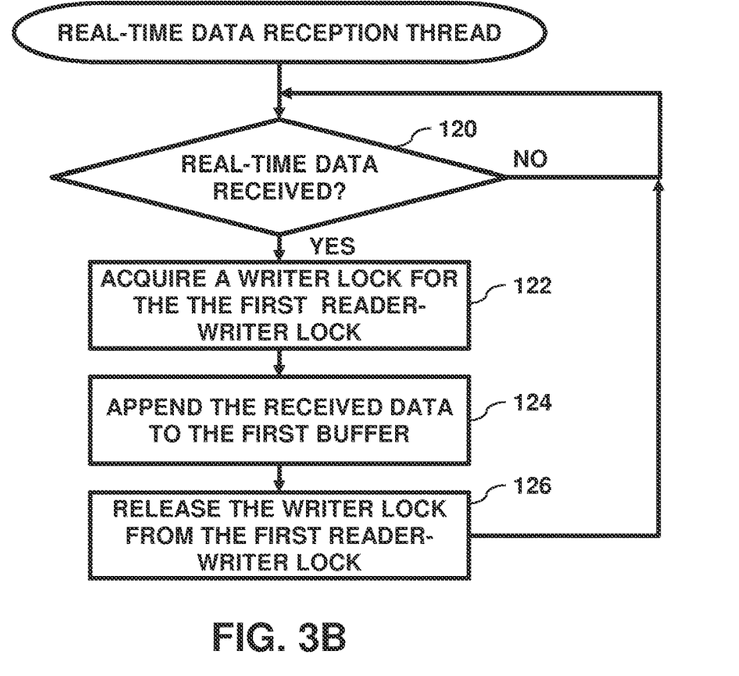

FIG. 3B is a flow diagram that schematically illustrates steps executed in the real-time data reception thread, in accordance with an embodiment of the present invention. In a first comparison step 120, processor 40 waits to receive real-time EP data 48. Upon receiving a stream of real-time EP data 48, processor 40, in an acquisition step 122, acquires a writer lock for RW lock 84A (i.e., to protect the first buffer). In an append step 124, processor 40 appends the received stream of real-time EP data 48 to the first buffer data. Finally, in a release step 126, processor 40 releases the writer lock from RW lock 84A, and the method continues with step 120.

Figure 3C:
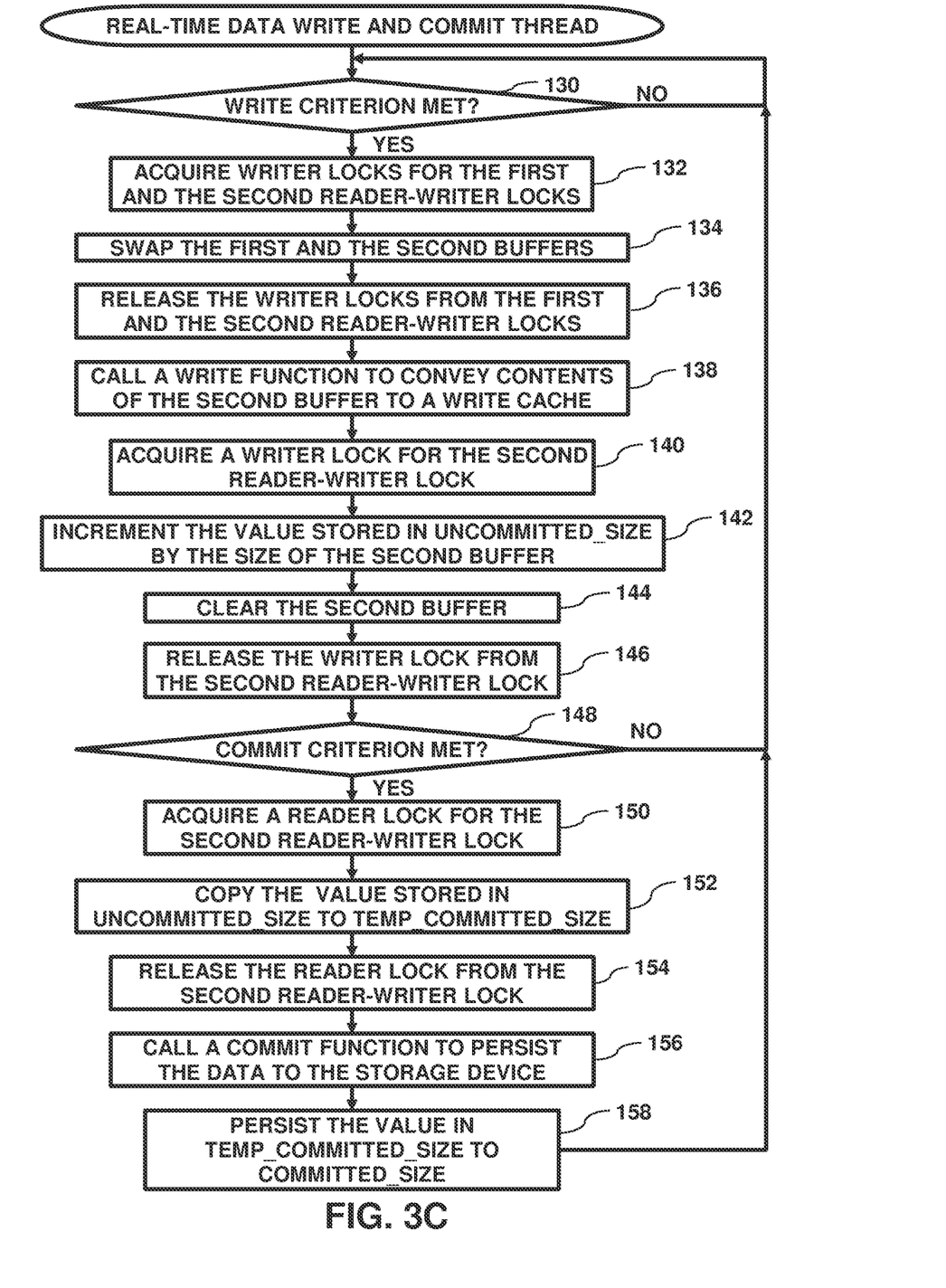

FIG. 3C is a flow diagram that schematically illustrates steps executed in the real-time data write and commit thread, in accordance with an embodiment of the present invention. In a first comparison step 130, processor 40 waits until a write criterion is met. The write criterion may comprise the first buffer comprising a first specific amount of data (e.g., one megabyte) or a first specific time period since processor 40 last called write function 70 (e.g., 20 seconds).

Upon identifying the write criterion being met, processor 40 acquires a first writer lock for RW lock 84A and a second writer lock form RW lock 84B in a first acquisition step 132, and in a swap step 134, the processor swaps the first and the second buffers by swapping the first buffer data in the first buffer with the second buffer data in the second buffer. In some embodiments the first buffer is stored at a first address in memory 62 referenced by buffer pointer 68A, the second buffer is stored at a second address in the memory referenced by buffer pointer 68B, and to swap the first buffer data in the first buffer with the second buffer data in the second buffer, processor 40 "toggles" the address stored in buffer pointer 68A between the first and the second addresses (i.e., swaps the addresses stored in buffer pointers 68A and 68B), thereby switching roles of the first and the second buffers.

For example, if buffer pointer 68A currently points to buffer 66A, processor 40 stores an address for buffer 66B to buffer pointer 68A in order to swap the first buffer data in the first buffer with the second buffer data in the second buffer. Likewise, if buffer pointer 68A currently points to buffer 66B, processor 40 stores an address for buffer 66A to buffer pointer 68A in order to swap the first buffer data in the first buffer with the second buffer data in the second buffer.

Upon swapping the first buffer data in the first buffer with the second buffer data in the second buffer, the stream of real-time EP data received in embodiments described hereinabove is stored in the second buffer, and processor 40 can execute the real-time data reception thread to store an additional stream of real-time EP data 48 to the first buffer. In a first release step 136, processor 40 releases the first writer lock from RW lock 84A and releases the second writer lock from RW lock 84B, and in a write step 138, the processor calls write function 70 to convey the second buffer data from the second buffer to write cache 72.

In a second acquisition step 140, processor 40 acquires a third writer lock for RW lock 84B, and in an increment step 142, the processor increments uncommitted_size 78 by a size of the second buffer data stored in the second buffer. In a clear step 144, processor 40 clears the second buffer, and in a second release step 146, the processor releases the third writer lock from RW lock 84B.

In the alternative embodiment described supra where RW lock 84C protects uncommitted_size 78, processor 40 acquires a fourth writer lock for RW lock 84C in step 140 and the processor releases the fourth writer lock from RW lock 84C in step 146. In the alternative embodiment, the third writer lock acquired for RW lock 84B in step 140 protects the second buffer.

In a second comparison step 148, processor 40 checks to see if a commit criterion is met. The commit criterion may comprise the first buffer comprising a second specific amount of data (e.g., two megabytes) or a second specific time period since processor 40 last called commit function 74 (e.g., 40 seconds).

If the commit criterion has been met, then processor 40 acquires a reader lock for RW lock 84B in a third acquisition step 150, copies the value stored in uncommitted_size 78 to temp_committed_size 80 in a copy step 152, and releases the reader lock from RW lock 84B in a third release step 154. In the alternative embodiment described supra where RW lock 84C protects uncommitted_size 78, processor 40 acquires the reader lock for RW lock 84C in step 150, and releases the reader lock from RW lock 84C in step 154.

In a commit step 156, processor 40 calls commit function 74 to persist (i.e., destage), to file 76 on storage device 64, the stream of real-time EP data currently stored in write cache 72. There may be instances where an operating system (not shown) executing on processor 40 has already destaged the real-time EP data from write cache 72 to file 76. In these instances, processor 40 can skip step 156.

Finally, in a persist step 158, processor 40 persists the value stored in temp_committed_size 80 to committed_size 88, and the method continues with step 130. To persist the value stored in temp_committed_size 80 to committed_size 88, processor 40 can call write function 70 to convey the value to write cache 72, and call commit function 74 to destage to the value to committed_size 88. Returning to step 148, if the commit criterion has not been met, then the method continues with step 130.

Figure 3D:
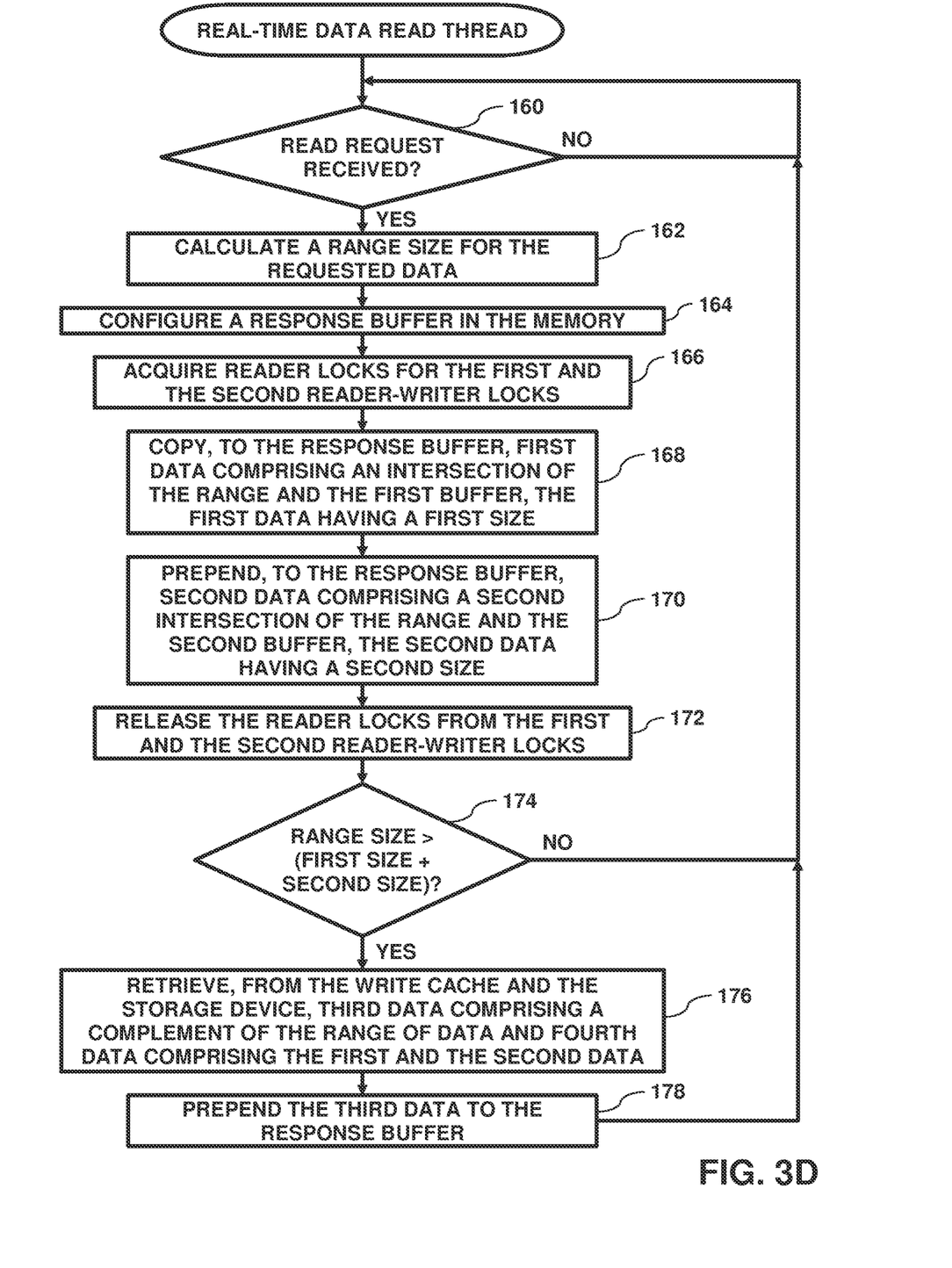

FIG. 3D is a flow diagram that schematically illustrates steps executed in the real-time data read thread, in accordance with an embodiment of the present invention. In embodiments described herein, the real time data thread is configured to process a read request for a range real-time EP data 48 that is currently stored in either:

The first buffer.
The first buffer and the second buffer.
The first buffer, the second buffer, and write cache 72 and/or file 76.
The second buffer.
The second buffer, and write cache 72 and/or file 76.
Write cache 72 and/or file 76.

In a first comparison step 160, processor 40 waits to receive a read request, and upon the processor 40 receiving a read request to retrieve a range of real-time EP data 48, the processor calculates a range size for the range of requested data in a calculation step 162, and configures response buffer 82 in memory 62 in a configuration step 164. To configure response buffer 82, processor 40 allocates, to the response buffer, a block of memory 62 whose size is in accordance with the calculated range size.

In an acquisition step 166, processor 40 acquires a first reader lock for RW lock 84A and acquires a second reader lock for RW lock 84B. In a copy step 168, processor 40 copies, to response buffer 82, first data comprising a first intersection of the requested range and the first buffer, the first data having a first size. In instances where the first buffer does not store any of the real-time EP in the requested range, then the first data comprises an empty subset and the first size is zero.

In a first prepend step 170, processor 40 prepends, to response buffer 82, second data comprising a second intersection of the requested range and the second buffer, the second data having a second size. In instances where the second buffer does not store any of the real-time EP in the requested range, then the second data comprises an empty subset and the second size is zero.

In a release step 172, processor 40 releases the first reader lock from RW lock 84A and releases the second reader lock from RW lock 84B. In a comparison step 174, if the range size is greater than a sum of the first and the second sizes, then in a retrieval step 176, processor 40 retrieves third data comprising a complement of the requested range and fourth data comprising the first and the second data.

In a second prepend step 178, processor 40 prepends the third data to response buffer 82, and the method continues with step 160. In some embodiments, upon completing to populate response buffer 82 (either in step 170 or step 176) processor 40 can convey a response to the read request indicating an address of response buffer 82. In an alternative embodiment, the response may comprise response buffer 82. Returning to step 174, if the range size is less than or equal to than the sum of the first and the second sizes, then the method continues with step 160.

As described supra, embodiments of the present invention receive and persist, to storage device 64, real-time EP data using atomic transactions. In embodiments described hereinabove, a given atomic transaction begins at step 120 in FIG. 3B and ends at step 178 in FIG. 3D.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for collecting, storing and processing real-time electrophysiological (EP) data, comprising:
  (a) providing a probe comprising a position sensor and an electrode at a distal end of the probe;
  (b) inserting the distal end of the probe in a heart of a patient during a medical procedure;
  (c) mapping electrical potentials and collecting EP data from the heart of the patient during the medical procedure using the electrode of the probe;
  (d) generating signals indicative of a location and orientation of the distal end of the probe in the heart of the patient during the medical procedure using the position sensor;
  (e) configuring, in a memory, a first buffer to store first buffer data, a second buffer to store second buffer data, and a variable indicative of a persisted size of the real-time data persisted to a storage device;
  (f) configuring, on the storage device, a file to store the real-time data and a field to store the variable, the file consisting of a confirmed data portion and an unconfirmed data portion;
  (g) receiving, by a processor, a stream of the real-time data comprising the signals generated from the position sensor;
  (h) determining location and orientation coordinates of the distal end of the probe
  (i) appending the stream of the real-time data to the first buffer data;
  upon meeting a write criteria:
    swapping the first buffer data in the first buffer with the second buffer data in the second buffer and swapping the second buffer data in the second buffer with the first buffer data in the first buffer;
    adding a buffer size of the second buffer data in the second buffer to the variable; and
    calling a write function to convey the second buffer data from the second buffer to a write cache; and
  upon meeting a commit criteria:
    calling a commit function to append the stream of the real-time data stored in the write cache to the file; and
    persisting the variable to the field, and
    calling the commit function again to ensure that the variable is persisted in case of a power loss, so that the field is indicative of the size of the confirmed data portion only and not indicative of the unconfirmed data portion; and
  (j) configuring a first reader-writer lock to protect the first buffer a second reader-writer lock to protect the second buffer and a third reader-writer lock to protect the variable,
  (k) acquiring a writer lock for the first reader-writer lock prior to appending the stream of the real-time data, and
  (l) releasing the writer lock from the first reader-writer lock subsequent to appending the stream of the real-time data,
  wherein the EP data is selected from the group consisting of analog data and digital data,
  wherein the first buffer is stored at a first address in the memory and the second buffer is stored at a second address in the memory, and
  wherein swapping the first buffer data in the first buffer with the second buffer data in the second buffer comprises toggling a buffer address stored in a buffer pointer between the first and the second addresses, thereby switching roles of the first and the second buffers,
  further comprising the steps of:
  upon receiving a request to retrieve a range of the real-time data: calculating a range size for the range,
    configuring, in the memory, a response buffer,
    acquiring a first reader lock for the first reader-writer lock and a second reader lock for the second reader-writer lock,
    copying first data comprising the range of real-time data held in the first buffer, to the response buffer,
    prepending second data comprising the range of real-time data held in the second buffer, to the response buffer,
    releasing the first and the second reader locks, and
    upon the range size being greater than a sum of the first and the second sizes:
      retrieving, from the write cache and the storage device, third data comprising a complement of the range and fourth data comprising the first data and the second data, and prepending the third data to the response buffer,
wherein the step of configuring, in the memory, the response buffer, occurs prior to completion of the step of prepending the third data to the response buffer, and
wherein to configure response buffer, the processor allocates, to the response buffer, a block of memory whose size is in accordance with the calculated range size,
wherein persisting the variable to the field comprises:
acquiring a third reader lock for the third reader-writer lock, copying the variable to an additional variable, releasing the reader lock, and
storing the additional variable to the field.

2. The method according to claim 1, wherein the analog data is selected from a list comprising voltages, currents and temperatures.

3. The method according to claim 1, and comprising:
acquiring the first writer lock for the first reader-writer lock and the second writer lock for the second reader-writer lock upon meeting the write criterion and prior to swapping the first and the second buffers, and
releasing the first and the second writer locks upon swapping the first buffer data in the first buffer with the second buffer data in the second buffer.

4. The method according to claim 1, and comprising:
acquiring the second writer lock for the second reader-writer lock subsequent to calling the write function and prior to adding the buffer size to the variable,
clearing the second buffer, and
releasing the writer lock upon clearing the second buffer.

5. The method according to claim 1, and comprising:
acquiring the first writer lock for the first reader-writer lock prior to appending the stream of the real-time data, and
releasing the writer lock from the first reader-writer lock subsequent to appending the stream of the real-time data.

6. The method according to claim 1, and comprising:
acquiring the first writer lock for the first reader-writer lock and the
second writer lock for the second reader-writer lock upon meeting the write criterion and prior to swapping the first buffer data in the first buffer with the second buffer data in the second buffer, and
releasing the first and the second writer locks upon swapping the first buffer data in the first buffer with the second buffer data in the second buffer.

7. The method according to claim 1, and comprising:
acquiring the second writer lock for the second reader-writer lock and the third writer lock for the third reader-writer lock subsequent to calling the write function and prior to adding the buffer size to the variable,
clearing the second buffer, and
releasing the first and the second writer locks upon clearing the second buffer.

8. An apparatus for collecting, storing and processing real-time electrophysiological (EP) data, comprising:
(a) a probe comprising a position sensor and an electrode at a distal end of the probe, the probe adapted for insertion in a heart of a patient during a medical procedure and for mapping electrical potentials and collecting EP data from the heart of the patient during the medical procedure using the electrode, the position sensor for generating signals indicative of a location and orientation of the distal end of the probe in the heart of the patient during the medical procedure; and
(b) a control console comprising:
(i) a storage device configured to store a file, and to store a field indicative of a persisted size of the real-time EP data persisted to the file, the file consisting of a confirmed data portion and an unconfirmed data portion;
(ii) a memory arranged to store a first buffer configured to store first buffer data, a second buffer configured to store second buffer data, and to store a variable indicative of the persisted size; and
(iii) a processor configured:
to receive the signals generated from the position sensor and determine location and orientation coordinates of the distal end of the probe,
(1) to receive a stream of the real-time EP data, the real-time EP data comprising the signals generated from the position sensor and determine location and orientation coordinates of the distal end of the probe,
(2) to append the stream of the real-time data to the first buffer data, upon meeting a write criteria:
to swap the first buffer data in the first buffer with the second buffer data in the second buffer and to swap the second buffer data in the second buffer with the first buffer data in the first buffer,
to add a buffer size of the second buffer data in the second buffer to the variable, and
to call a write function configured to convey the second buffer data from the second buffer to a write cache, and upon meeting a commit criteria:
to call a commit function configured to append the stream of the real-time EP data stored in the write cache to the file, and
to persist the variable,
wherein the EP data is selected from analog data and digital data,
wherein the processor is configured to store the first buffer at a first address in the memory, to store the second buffer at a second address in the memory, and to swap the first buffer data in the first buffer with the second buffer data in the second buffer by toggling a buffer address stored in a buffer pointer between the first and the second addresses, thereby switching roles of the first and the second buffers,
wherein the processor is arranged to configure a first reader-writer lock to protect the first buffer, and to configure a second reader-writer lock to protect the second buffer and to configure a third reader-writer lock to protect the variable, and
wherein the processor is configured:
to acquire a writer lock for the first reader-writer lock prior to appending the stream of the real-time data, and
to release the writer lock from the first reader-writer lock subsequent to appending the stream of the real-time data
wherein upon receiving a request to retrieve a range of the real-time data, the processor is arranged:
to calculate a range size for the range, to configure, in the memory, a response buffer,
to acquire a first reader lock for the first reader-writer lock and a second reader lock for the second reader-writer lock,
to copy first data comprising the range of real-time data held in the first buffer, to the response buffer,
to prepend second data comprising the range of real-time data held in the second buffer, to the response buffer,
to release the first and the second reader locks, and
upon the range size being greater than a sum of the first and the second sizes:

to retrieve, from the write cache and the storage device, third data comprising a complement of the range and fourth data comprising the first data and the second data, and
to prepend the third data to the response buffer,
wherein the processor is adapted so that the configuring, in the memory, the response buffer, occurs prior to completion of prepending the third data to the response buffer, and
wherein to configure response buffer, the processor is adapted to allocate, to the response buffer, a block of memory whose size is in accordance with the calculated range size.

9. The apparatus according to claim 8, wherein the analog data is selected from a list comprising voltages, currents and temperatures.

10. The apparatus according to claim 8, wherein the digital data is selected from a list comprising image data, position measurements, force measurements and respiration statuses.

11. The apparatus according to claim 8, wherein the processor is configured:
to acquire the first writer lock for the first reader-writer lock and the second writer lock for the second reader-writer lock upon meeting the write criterion and prior to swapping the first and the second buffers, and
to release the first and the second writer locks upon swapping the first buffer data in the first buffer with the second buffer data in the second buffer.

12. The apparatus according to claim 8, wherein the processor is configured:
to acquire the second writer lock for the second reader-writer lock subsequent to calling the write function and prior to adding the buffer size to the variable,
to clear the second buffer, and
to release the writer lock upon clearing the second buffer.

13. The apparatus according to claim 8, wherein the processor is configured to persist the variable to the field by:
acquiring the second reader lock for the second reader-writer lock,
copying the variable to the additional variable,
releasing the reader lock, and
storing the additional variable to the field.

14. The apparatus according to claim 8, wherein the processor is arranged to configure a first reader-writer lock to protect the first buffer, to configure a second reader-writer lock to protect the second buffer, and to configure a third reader-writer lock to protect the variable.

15. The apparatus according to claim 14, wherein the processor is configured:
to acquire a writer lock for the first reader-writer lock prior to appending the stream of the real-time data, and
to release the writer lock from the first reader-writer lock subsequent to appending the stream of the real-time data.

16. The apparatus according to claim 14,
wherein the processor is configured:
to acquire the first writer lock for the first reader-writer lock and the second writer lock for the second reader-writer lock upon meeting the write criterion and prior to swapping the first buffer data in the first buffer with the second buffer data in the second buffer, and
to release the first and the second writer locks upon swapping the first buffer data in the first buffer with the second buffer data in the second buffer.

17. The apparatus according to claim 14, wherein the processor is configured:
to acquire the second writer lock for the second reader-writer lock and the third writer lock for the third reader-writer lock subsequent to calling the write function and prior to adding the buffer size to the variable,
to clear the second buffer, and
to release the first and the second writer locks upon clearing the second buffer.

18. The apparatus according to claim 14, wherein the processor is configured to persist the variable to field the by:
acquiring a third reader lock for the third reader-writer lock, copying the variable to an additional variable, releasing the reader lock, and
storing the additional variable to the field.

19. The method according to claim 1, wherein the write cache is flushed before persisting the variable to the field and wherein the write cache is flushed after persisting the variable to the field.

20. The method according to claim 1, wherein the commit function is called a second time to flush to a disk.

21. The apparatus according to claim 8, wherein the write cache is flushed before persisting the variable to the field and wherein the write cache is flushed after persisting the variable to the field.

22. The apparatus according to claim 8, wherein said commit function is called a second time to flush to a disk.

23. The apparatus according to claim 8, wherein the commit function is called a second time to flush to a disk.

* * * * *